United States Patent

Reitmeier et al.

Patent Number: 5,889,198
Date of Patent: Mar. 30, 1999

[54] METHOD FOR DETECTING AND MEASURING $CH_4$ WITH $GA_2O_3$ SENSOR

[75] Inventors: Norbert Reitmeier, Munich; Maximilian Fleischer, Hoehenkirchen; Hans Meixner, Haar, all of Germany

[73] Assignee: Siemens Aktiengesellschaft, Munich, Germany

[21] Appl. No.: 853,927

[22] Filed: May 9, 1997

[30] Foreign Application Priority Data

May 9, 1996 [DE] Germany ................ 196 18 705.2

[51] Int. Cl.⁶ .................................................. G01N 25/00
[52] U.S. Cl. .............................. 73/25.05; 73/31.05
[58] Field of Search ........................ 73/23.21, 25.01, 73/25.05, 31.05

[56] References Cited

U.S. PATENT DOCUMENTS

| 4,045,729 | 8/1977 | Loh | 73/31.05 |
| 4,057,996 | 11/1977 | Firth et al. | 73/310.5 |
| 5,767,388 | 6/1998 | Fleischer et al. | 73/310 |

FOREIGN PATENT DOCUMENTS 44 28 155 A1  9/1994  Germany.

OTHER PUBLICATIONS

"Algorithms to Improve the Selectivity of Thermally-Cycled Tin Oxide Gas Sensors", by W.M. Sears et al., Sensors and Actuators, vol. 19 (1989), pp. 333–349.

"Selective Thermally Cycled Gas Sensing Using Fast Fourier–transform Techniques", by W.M. Sears et al., Sensors and Acutators B, vol. 2 (1900), pp. 283–289.

"Signal–shape Analysis of a Thermally Cycled Tin–oxide Gas Sensor", by Stanislaw Wlodek et al., Sensors and Actuators B, vol. 3 (1991), pp. 63–68.

Primary Examiner—Max H. Noori
Attorney, Agent, or Firm—Hill & Simpson

[57] ABSTRACT

A method for detecting $CH_4$ with a $Ga_2O_3$ sensor, and a method for measuring $CH_4$ concentration with a $Ga_2O_3$ sensor is provided. In order to solve the problem associated with the masking or disturbing effect alcohol has on the detection of methane with a gallium oxide detector, the present invention provides a method where the sensor conductivity $((G(t_1))$ is acquired at a first sensor temperature, and is compared with a first threshold value. If the conductivity $((G(t_1))$ exceeds this threshold value, it is determined that alcohol is present in the gas mixture to be examined. The sensor is then heated, and a second conductivity $(G(t_2))$ is acquired. If the ratio of the second to the first conductivity exceeds a second threshold value, $CH_4$ is likewise present in the gas mixture. The measurement of the $CH_4$ concentration ensues by means of an acquisition of two conductivities $(G(t_1), G(t_2))$ at different temperatures. The corresponding $CH_4$ value can be taken from a table or reference plot.

17 Claims, 3 Drawing Sheets

FIG. 3b

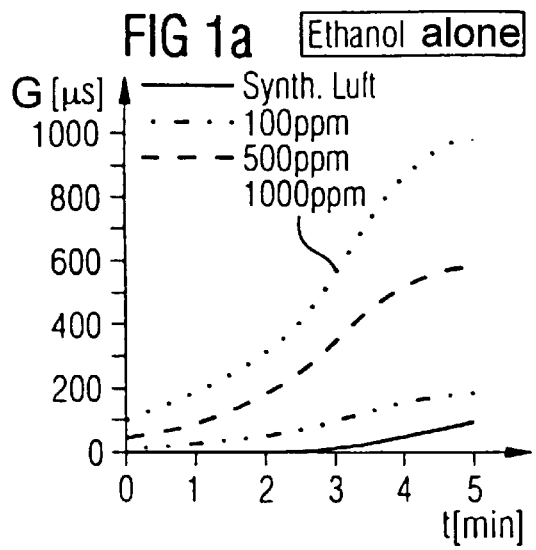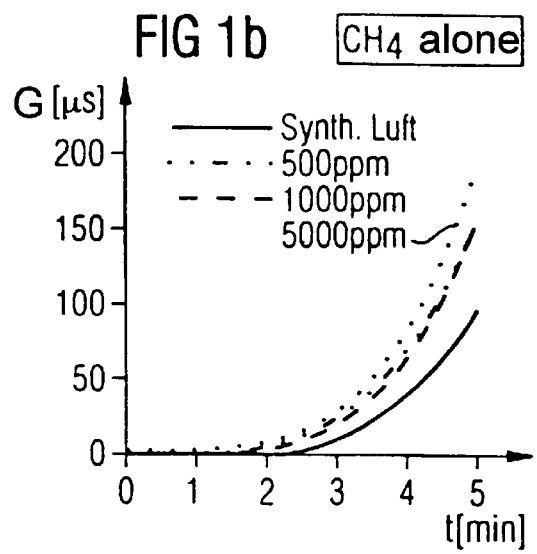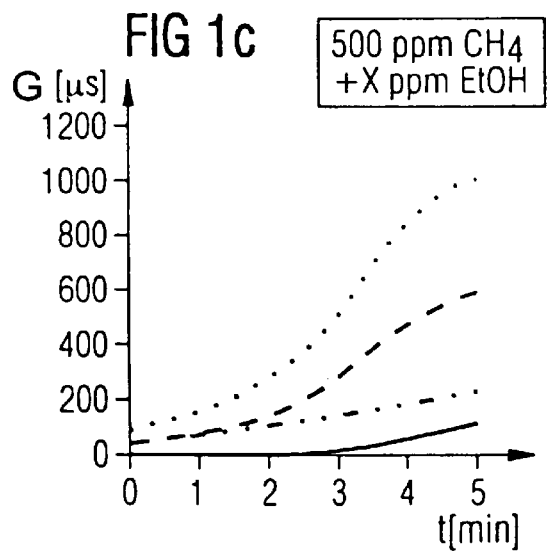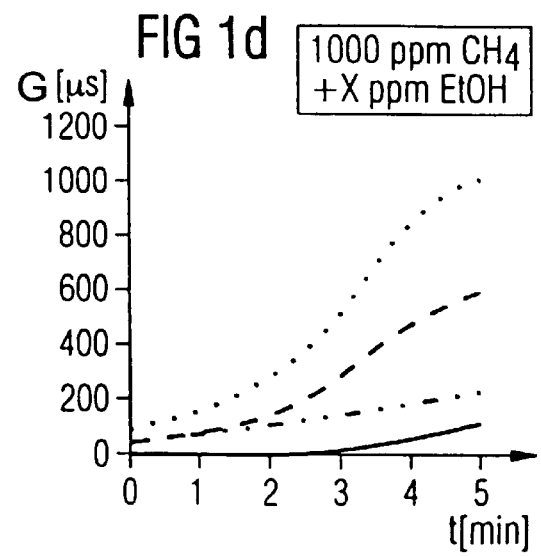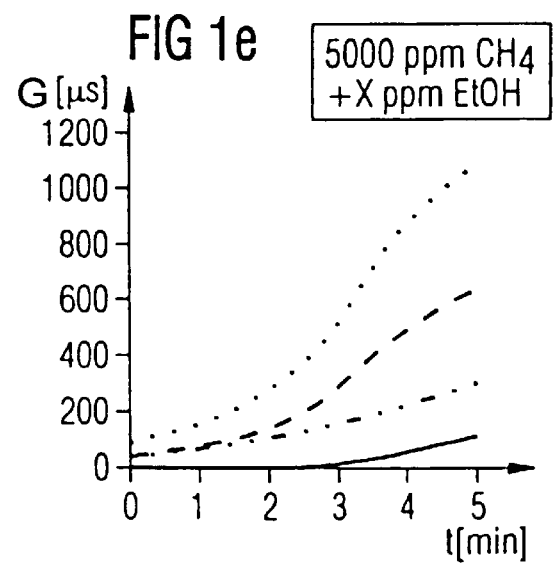

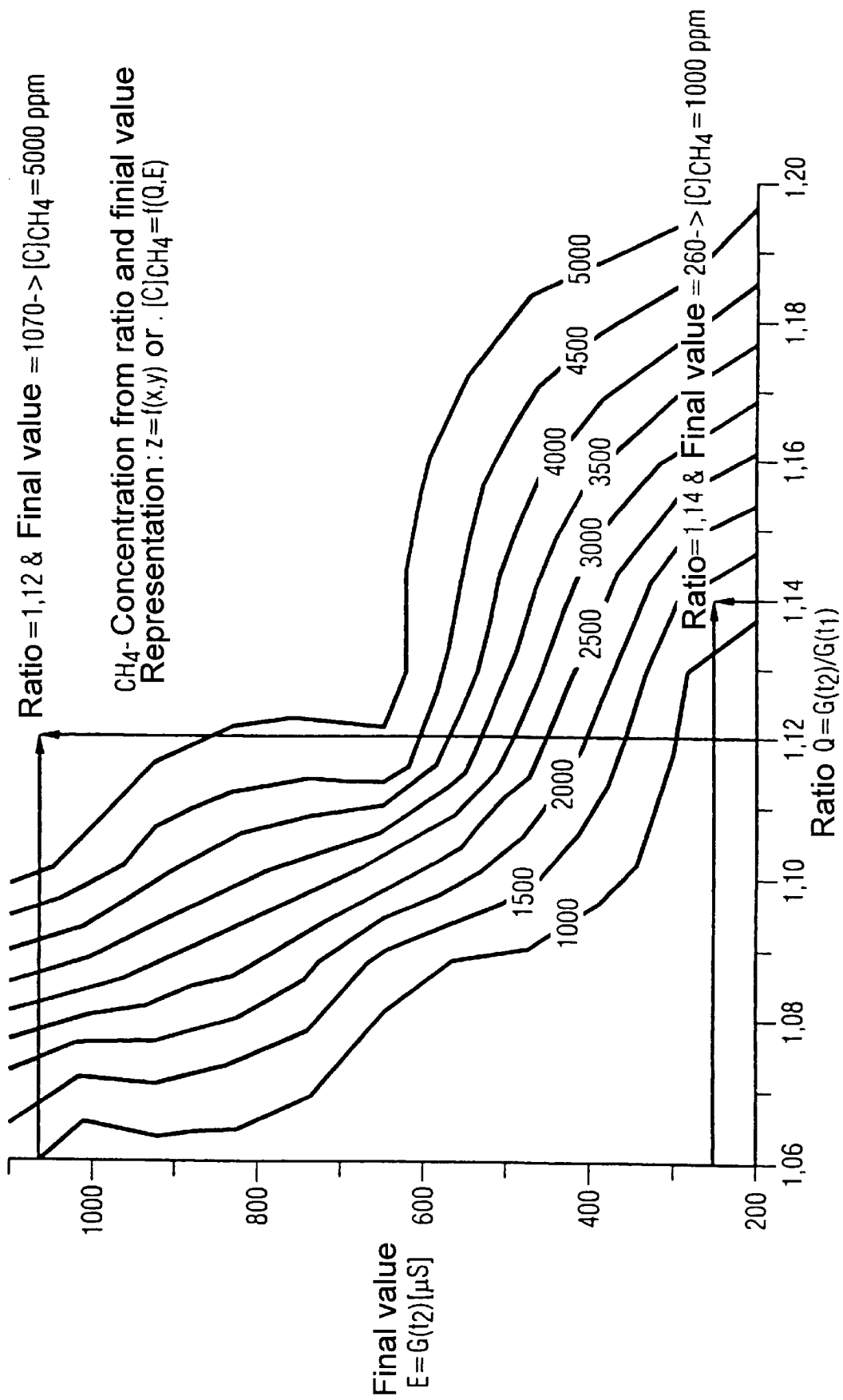

METHOD FOR DETECTING AND MEASURING CH$_4$ WITH GA$_2$O$_3$ SENSOR

BACKGROUND OF THE INVENTION

The present invention relates generally to methane detectors, methods of detecting methane in a gas mixture, methane concentration measuring devices and methods of measuring methane concentration in a gas mixture.

A serious problem in the use of gas sensors based on gallium oxide (Ga$_2$O$_3$) films is that, given the simultaneous presence of several gases, the sensor signal is composed of the superposition of all present gas components with the same characteristics, e.g., all present gas components have a reducing effect. This behavior, generally called cross-sensitivity, poses a serious obstacle to the effective operation of methane warning systems or methane measurement devices based on sputtered semiconducting Ga$_2$O$_3$ layers.

For example, given the simultaneous presence of methane and alcohol vapor or, respectively, solvent vapors, the lack of selectivity of the sensor elements causes an ambiguity of the sensor signal, and thus to false alarms of the detector. Or, a methane concentration is measured that deviates significantly from the actual methane concentration. Since the sensitivity S of the Ga$_2$O$_3$ sensors to the more reactive components, i.e. the alcohol vapors or, respectively, solvent vapors, is very high (typically about one order of magnitude higher than to the less reactive gases), an additional reducing gas component, e.g. methane, cannot be detected with sufficient sensitivity.

Up to now, several solutions have been proposed for improving the selectivity of methane gas sensors based on Ga$_2$O$_3$.

In the German patent DE 41 39 721, an arrangement is provided for the detection of gases and a method is known for the selective detection of at least one gas contained in a gas mixture. For the selective detection of at least one gas contained in a gas mixture, the operating temperature of the gas sensor is varied. The time curve of a signal that depends on the electrical conductivity of the sensor layer is evaluated. For this purpose, the operating temperature of the gas sensor is increased in a leap, and the time curve of the sensor signal is registered. The evaluation ensues by means of a Fourier transformation. A disadvantage of this method is the relatively large expense for the evaluation by means of the Fourier transformation.

The company SATE of Salerno, Italy, uses a method in which the CH$_4$ sensor is operated for a certain time at a first temperature and operated for a certain time at a second temperature. This process is repeated periodically. Using this method, it is possible to avoid false alarms of the methane detector. However, the presence of methane in a gas mixture containing alcohol or solvent vapors cannot be detected using this sensor.

A method for selective gas detection is known from the prior art Sears et al., Selective Thermally Cycled Gas Sensing Using Fast Fourier-Transform Techniques, Sensors and Actuators B, 2 (1990), pp. 283–289. A fast Fourier transformation (FFT) is used for the analysis of the data. This method has the disadvantage that a high computing expense is required for the evaluation.

A method for the analysis of gas mixtures is known from the prior art Wlodek, S. et al., Signal-Shape Analysis of a Thermally Cycled Tin-Oxide Gas Sensor, Sensors and Actuators B, 1991, pp. 63–68. The function of change of conductivity over time is simulated by several summed Gauss functions. The indices of the Gauss functions represent characteristic features for the gases respectively present in the gas mixture. A considerable computing expense is also required here for the evaluation.

A method for determining the concentration of a single gas using an SnO$_2$ gas sensor is known from the prior art Sears, W., et al., Algorithms to improve the selectivity of thermally-cycled tin oxide gas sensors, Sensors and Actuators, 1989, pp. 333–349. For this purpose, the conductivity is measured dependent on sensor temperature and time. For different gases, the result different sensor signal curves dependent on the concentration of the gas. However, a disadvantage of this method is that it can be used only for individual gases, i.e. this method cannot be used for a gas mixture consisting for example of air, methane and alcohol vapors.

Accordingly, there is a need for improved methane detectors, methods of detecting methane, methane concentration measuring devices and methods of measuring methane concentration that can overcome the problems associated with disturbing or masking gases such as solvents and which further provide accurate detection and measurement without requiring expensive equipment such as the expensive microprocessors required to perform the Fourier transformations, fast Fourier transformations and summation of Gauss functions required by the above-described methods.

SUMMARY OF THE INVENTION

The present invention provides a method for recognizing methane (CH$_4$) in a gas mixture that contains camouflaging or masking gases, such as solvent in the form of alcohol. The invention can be used in a methane warning or alarm apparatus. The present invention also provides a method for measuring the CH$_4$ concentration in a gas mixture containing disturbing gases. In relation to the first-named method, the second method is distinguished by a precise indication of the concentration of the methane.

An object of the present invention is to indicate a method that enables the indication with certainty of the concentration of a particular gas located in a gas mixture containing disturbing, masking or camouflaging gases.

The method of detecting methane with a galium oxide film sensor includes the steps of operating the sensor at a first temperature which generates a first sensor signal. The first sensor signal is compared with a first threshold value. If the first sensor signal is less than the first threshold value, the preceding steps are repeated and the sensor continues to be operated at the first temperature. If, however, the first sensor signal exceeds the first threshold value, the temperature of the sensor is increased to a second temperature. A first transient sensor signal is generated at a first time after the increase in temperature of the sensor and, thereafter, the second transient sensor signal is generated at a second time or an elapsed time after the first time when the first transient sensor signal is generated. A ratio of the second transient sensor signal to the first transient sensor signal is calculated and compared with a second threshold value. If the ratio is below the second threshold value, the method is begun again and no methane has been detected. However, if the ratio is above a second threshold value, methane has been detected and an appropriate methane-indicating signal is generated.

In an embodiment, the temperature of the sensor is increased by increasing a heating voltage across the sensor.

In an embodiment, the elapsed time between the first and second times is about 5 minutes.

In an embodiment, the elapsed time between the first and second times is less than 5 minutes.

In an embodiment, the elapsed time between the first and second times is about 30 seconds.

In an embodiment, the signal generated upon detection of methane is an alarm.

In a related embodiment, the alarm is automatically turned off if the ratio falls below the second threshold value.

In yet another embodiment, the alarm must be turned off manually.

In an embodiment, after the first sensor signal is determined to exceed the first threshold value and the temperature of the sensor is increased, the sensor signal recorded after the increase in temperature is differentiated by means of an operational amplifier. The differentiated sensor signal is then compared with a second threshold value. If the differentiated sensor signal is greater than the second threshold value, a methane present signal is generated. If the differentiated sensor signal is less than the second threshold value, the process is repeated beginning with the step of operating the sensor at the first lower temperature and generating the first sensor signal.

In an embodiment, the method of the present invention provides a means for measuring the methane concentration in a gas using a galium oxide sensor. The method comprises the steps of operating the sensor at a first temperature, generating and recording a first sensor signal, increasing the temperature of the sensor to a second temperature, generating a second sensor signal, calculating a ratio of the second sensor signal to the first sensor signal and retrieving a methane concentration associated with the just-calculated ratio and the second sensor signal value from a stored set of values.

In an embodiment, the stored set of values is a graphical plot of methane concentration as a function of both the second sensor signal value and the calculated ratio.

In an embodiment, the stored set of values is stored on an EEPROM.

The invention has the advantage that the $CH_4$ detection or, respectively, the measurement of the concentration of $CH_4$ is possible with conventional gallium oxide sensors without modification of the sensor elements. The circuit outlay is small. An additional advantage is the elimination of batch variations. The aging of the sensor plays no role in the identification of gases.

BRIEF DESCRIPTION OF THE DRAWINGS

The invention is described more or less diagrammatically in the accompanying drawings, wherein:

FIG. 1a illustrates, graphically, the conductivity of air and air contaminated with various levels of ethanol in a time-dependent fashion as the detector is operated between two temperatures;

FIG. 1b illustrates, graphically, the conductivity of air and air contaminated with various levels of methane in a time-dependent fashion as the detector is operated between two temperatures;

FIG. 1c illustrates, graphically, the conductivity of air contaminated with 500 ppm methane and various concentrations of ethanol in a time-dependent fashion as the detector is operated between two temperatures;

FIG. 1d illustrates, graphically, the conductivity of air contaminated with 1,000 ppm methane and various concentrations of ethanol in a time-dependent fashion as the detector is operated between two temperatures;

FIG. 1e illustrates, graphically, the conductivity of air contaminated with 5000 ppm methane and various concentrations of ethanol in a time-dependent fashion as the detector is operated between two temperatures;

FIG. 2 illustrates, graphically, a method for determining the methane concentration in a gas mixture utilizing the calibration measurement of the present invention;

DETAILED DESCRIPTION OF THE PRESENTLY PREFERRED EMBODIMENTS

Figure 3A:
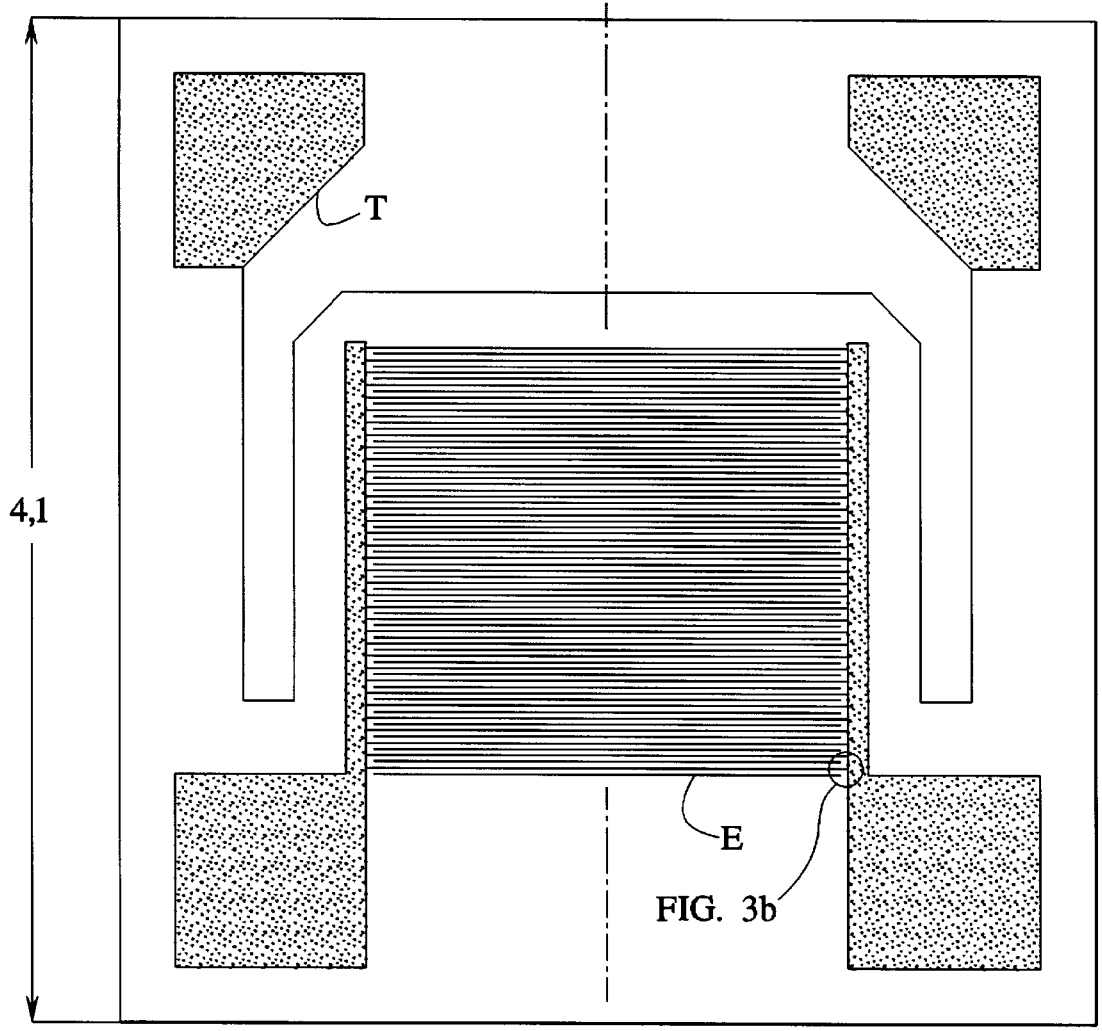
FIG. 3a is a top view of a gas sensor that can be used for the present invention.

A gas sensor based on $Ga_2O_3$ that can be used for this invention is known for example from pages 3–5 of P 44 28 155.2 which is incorporated herein by reference. Specifically, the sensor manufactured according to the inventive method has the construction shown in FIGS. 3a, 3b. The gas-sensitive layer A of $Ga_2O_3$ is applied on a substrate S, which consists for example of BeO, and on whose upper side is located an interdigital electrode structure E. In FIG. 3a, in addition a temperature sensor T surrounding the sensor structure is shown. The sensor construction is symmetrical with respect to the axis Sym. All dimensions in FIG. 3a are given in millimeters.

Figure 3B:
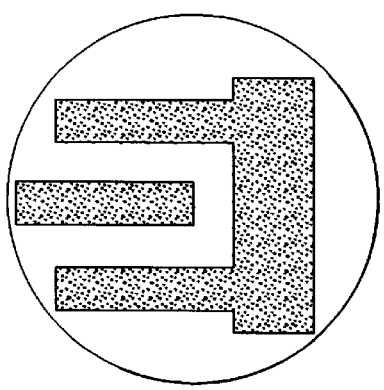
FIG. 3b is a side view of a gas sensor that can be used for the present invention.
Figure 3C:
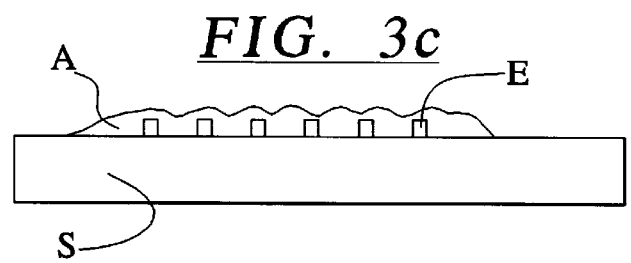
FIGS. 3c–d is a side view of a gas sensor that can be used for the present invention.
Figure 3D:
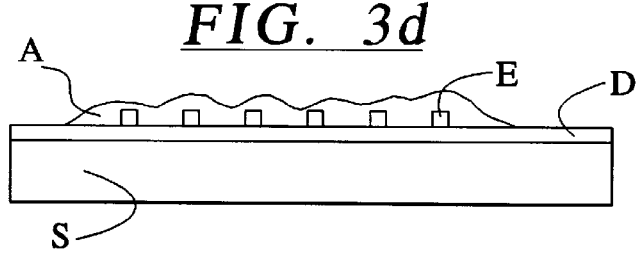

In the construction shown in FIG. 3c, a diffusion blocking layer D is first applied on the substrate S. The diffusion blocking layer D contains a silicon compound such as silicon oxide, silicon nitride or silicon oxinitride. In a next step, the interdigital electrode structure E is arranged on this layer. Finally, as in the construction shown in FIG. 3b, the gas-sensitive layer A is deposited.

If the construction of the gas-sensitive layer A takes place by means of reactive sputtering, the sputter gas is preferably a gas mixture of Ar with 10 to 25% oxygen. During the deposition process, the substrate S is heated to approximately 500° C.

Further possibilities for the application of the gas-sensitive layer include molecular beam epitaxy, thermal vapor deposition, or a screen printing method.

In the manufacturing method, to which the construction shown in FIG. 3b corresponds, after the application of the gas-sensitive layer there takes place the tempering at approximately 750°–850° C., preferably at 800° C. This tempering process is carried out for approximately 5–20 h, preferably 10 h. The exact temperature and tempering duration are determined by means of the desired application of the gas sensor. If the operating temperature of the gas sensor is 750° C., the tempering process should be carried out at approximately 800° C. In general, the tempering temperature should lie approximately 50° C. or more above the desired operating temperature of the gas sensor.

By means of the tempering at approximately 750°–850° C., as well as the diffusion blocking D, it is achieved that the $Ga_2O_3$ layer of the sensor is acceptor-free. 'Acceptor-free' means here that the semiconductor comprises no impurities that could trap electrons. Impurities in the semiconductor would have an adverse effect on the conductivity.

A gas sensor constructed according to FIG. 3c can be operated at temperatures up to 1200° C. while maintaining its good characteristics such as high conductivity and sensitivity.

The invention removes the alcohol cross-sensitivity of the $Ga_2O_3$ sensor through the use of a specific evaluation method. The sensor is not (as is known from the conventional mode of operation of resistive gas sensors) operated at a constant temperature of use (i.e. heating voltage), optimized for the gas components to be detected, but rather is operated transiently between two different temperatures. The time-dependent conductivity curves G(t) obtained in this way are processed digitally.

The gallium oxide-based methane sensor is operated for a determined time duration at its temperature of use, typically 850° C. (=θ1). If the sensor conductivity $G_S$ received from the sensor exceeds a threshold value $SW_{EtOH}$, which means that alcohol or solvent vapors have been detected, the sensor is heated from its use temperature θ1 to a temperature θ2=1050° C. in a temperature-transient cycle. For testing purposes, the heating process lasted five minutes. However, in practice the cycle duration $t_{cycle}$ can be reduced to about 30 seconds.

In FIGS. 1a–1e, the cycle duration plotted on the x axis is five minutes. The detection of methane against the background of a level of alcohol or, respectively, solvent is illustrated in FIGS. 1a–1e, using the example of methane/ethanol mixtures.

FIGS. 1a to 1e respectively show the transient conductivity G(t), plotted on the y axis in $\mu S$, in relation to time t, plotted on the x axis in minutes.

FIG. 1a shows the curves of the sensor conductivities G from bottom to top for synthetic air, 100 ppm, 500 ppm and 1000 ppm ethanol. At the end of the five-minute heating process, a conductivity G(t=5 min) of 972.8 $\mu S$ arises for example for a concentration of 1000 ppm ethanol. In contrast, at the beginning of the measurement, at the same ethanol concentration, there was a conductivity G(t=0 min) of 100 $\mu S$.

FIG. 1b shows the curves of the sensor conductivities G for synthetic air (corresponds to the sensor signal curve in FIG. 1a) for 500 ppm, 1000 ppm and 5000 ppm $CH_4$. Ethanol is not present in this gas mixture. It can be seen that after five minutes a sensor conductivity G(t=5 min) of 200 $\mu S$ arises at 5000 ppm $CH_4$. It can be seen clearly that the sensor reacts considerably more weakly to $CH_4$ than to ethanol.

FIG. 1c shows sensor conductivities G for gas mixtures that contain 500 ppm $CH_4$ and 100 ppm, 500 ppm or, respectively, 1000 ppm EtOH. At time t=5 min, given a mixture of 500 ppm $CH_4$ and 500 ppm EtOH, there results a conductivity G(t=5 min) of 587.9 $\mu S$. At time t=4.5 min, there arises a conductivity G(t=4.5 min) of 544.35 $\mu S$.

FIG. 1d shows the curves of the conductivities G for 1000 ppm $CH_4$ in connection with 100 ppm, 500 ppm or, respectively, 1000 ppm EtOH.

FIG. 1e shows the curves of the sensor values G for 5000 ppm $CH_4$ in connection with 100 ppm, 500 ppm or, respectively, 1000 ppm EtOH.

FIGS. 1a to 1e and the Table 1 presented below indicate that the increases in the conductivity curves G(t) of the $EtOH/CH_4$ mixtures towards the end of the cycle are larger than those from EtOH alone. This behavior is exploited in order to identify $CH_4$ unambiguously, given the simultaneous presence of alcohol vapors and solvent vapors. For the case of the cycle shown in FIGS. 1a–1e, with $t_{cycle}$=5 min, the quotient of G(t=5 min)/G(t=4.5 min) is used as a characteristic quantity. The values listed in the following table result:

TABLE 1

| [c] EtOH in ppm | G(t = 5 min)/ G(t = 4.5 min) with EtOH alone | G(t = 5 min)/ G(t = 4.5 min) with 500 ppm $CH_4$ + EtOH | G(t = 5 min)/ G(t = 4.5 min) with 1000 ppm $CH_4$ + EtOH | G(t = 5 min)/ G(t = 4.5 min) with 5000 ppm $CH_4$ + EtOH |
|---|---|---|---|---|
| 100 | 1.04 | 1.13 | 1.14 | 1.20 |
| 500 | 1.03 | 1.08 | 1.09 | 1.12 |
| 1000 | 1.01 | 1.06 | 1.07 | 1.10 |

As can be seen from Table 1, the quotients of G(t=5 min)/G(t=4.5 min) for mixtures of EtOH with $CH_4$ lie well above those of EtOH without $CH_4$. In this way, the presence of $CH_4$ can be detected clearly with the simultaneous presence of alcohol vapors, since a ratio of two conductivities is concerned, independent of batch variations (i.e. the absolute values of conductivities). The digital outlay for the evaluation is low, and can be realized with inexpensive commercially available microcontrollers (e.g., the SAB 80C537).

In the method for the detection of $CH_4$ by means of a gallium oxide sensor, the sensor is operated at a first temperature θ1 for a definite period of time, and its sensor conductivity $G_S$ is compared with a threshold value $SW_{EtOH}$. If the sensor value is under this threshold value $SW_{EtOH}$, the sensor continues to be operated at the first temperature θ1. However, if the sensor signal exceeds the first threshold value $SW_{EtOH}$, the sensor temperature is increased, and the corresponding conductivities $G(t_1)$ or, respectively, $G(t_2)$ are thereby acquired at two different times $t_1$ and $t_2$. The ratio of the sensor conductivity $G(t_2)$ and the sensor conductivity $G(t_1)$ is compared with a second threshold value $SW_{CH4}$. If the ratio is below the threshold value $SW_{CH4}$, the sensor is returned to the operating temperature θ1, and the sensor conductivity $G_S$ is acquired at the operating temperature θ1, as specified above. However, if the threshold value $SW_{CH4}$ is exceeded, this is evaluated as the presence of methane. If necessary, an alarm can be triggered.

The above steps are repeated periodically. According to the application, the alarm can also be maintained in the case of the subsequent reduction of the $CH_4$ concentration, falling again below the threshold value $SW_{CH4}$. Preferably, only manual actuation will reset the alarm. It is also possible to reset the triggered alarm automatically in this case. The case of application will determine which of these two variants will be used.

An alternative to the formation of the quotient $G(t_2)/G(t_1)$ consists in the differentiation of the sensor signal by means of an operational amplifier. In contrast to the formation of the ratio $G(t_2)/G(t_1)$, which is carried out discretely, the differentiation by means of an operational amplifier has the advantage of a continuous monitoring.

It is also possible to determine the $CH_4$ concentration precisely despite the presence of disturbing gases. The $Ga_2O_3$ sensor is operated at a first temperature θ1, and its sensor conductivity $G_S$ is recorded. The temperature of the sensor is subsequently increased, and a second sensor signal $G(t_2)$ is thereby acquired. The ratio is formed by computer from the two sensor conductivities $G(t_2)$ and $G_S$. The corresponding $CH_4$ value can be learned immediately from a two-dimensional lookup table or plot, in which the respective $CH_4$ concentration value is stored for the sensor conductivity $G(t_2)$ and the ratio of $G(t_2)$ to $G_S$. The table is to be calculated once, and can be stored in an EEPROM. The table can be obtained for example from a diagram as shown in FIG. 2. In FIG. 2, the sensor conductivity $G(t_2)$ occurring at time $t_2$ is plotted in $\mu S$ on the y axis. The quotient of $G(t_2)/G(t_S)$ or $G(t_2)/G(t_1)$ is plotted on the x axis.

The lines shown in the diagram result in dependence on the EtOH and $CH_4$ concentration. For example, it can be learned from FIG. 2 that, given a quotient of $G(t_2)/G(t_1)$ of 1.14 and a conductivity $G(t_2)$ of 260 $\mu S$, a $CH_4$ concentration of at least 1000 ppm is present. The diagram shown in FIG. 2 is a contour plot z=f(x,y) or, respectively, $[c]_{CH4}$=f(Q,E), i.e. the lines are lines of equal $CH_4$ concentrations. As can be seen from the diagram, with the knowledge of the quotient $G(t_2)/G(t_1)$ and of the conductivity $G(t_2)$ within the precision with which calibration took place, a $CH_4$ concentration can be allocated to each pair of values [$G(t_2)/G(t_1)$; $G(t_2)$]. Some absolute values for conductivities for different gas mixtures can be found in the following table.

| [c] EtOH in ppm | $G(t2)$ in $\mu S$ with pure EtOH | $G(t2)$ in $\mu S$ with 500 ppm $CH_4$ | $G(t2)$ in $\mu S$ with 1000 ppm $CH_4$ | $G(t2)$ in $\mu S$ with 5000 ppm $CH_4$ |
| --- | --- | --- | --- | --- |
| 100 | 182.0 | 241.6 | 260.1 | 303.5 |
| 500 | 569.5 | 587.9 | 618.4 | 637.3 |
| 1000 | 972.8 | 1005.0 | 1047.1 | 1070.0 |

In principle, in place of the conductivity G any other measurement quantity, such as sensor resistance or sensor signal, can also be used for the evaluation.

A linear increase in the temperature from $\theta 1$ to $\theta 2$ ensues advantageously by means of a linear increase in the heating voltage (typically 7–11 V).

From the above description, it is apparent that the objects and advantages of the present invention have been achieved. While only certain embodiments have been set forth, alternative embodiments and various modifications will be apparent from the above description to those skilled in the art. These and other alternatives are considered equivalents and within the spirit and scope of the present invention.

We claim:

1. A method for detecting $CH_4$ with a $Ga_2O_3$ sensor comprising the following steps:
   (a) operating the sensor at a first temperature ($\theta 1$) to generate a first sensor signal ($G_S$),
   (b) comparing the first sensor signal ($G_S$) with a first threshold value ($SW_{EtOH}$),
   (c) if the first sensor signal ($G_S$) is less than the first threshold value ($SW_{EtOH}$), repeating step (a), and
   if the first sensor signal ($G_S$) exceeds the first threshold value ($SW_{EtOH}$), executing step (d),
   (d) increasing the sensor temperature to a second temperature ($\theta 2$) and generating a first transient sensor signal ($G(t_1)$) at a first time ($t_1$) and a second transient sensor signal ($G(t_2)$) at a second time (t2), the second time ($t_2$) being later than the first time ($t_1$),
   (e) calculating a ratio of the second transient sensor signal ($G(t_2)$) to the first transient sensor signal ($G(t_1)$),
   (f) comparing the ratio with a second threshold value ($SW_{CH4}$),
   (g) if the ratio is below the second threshold value ($SW_{CH4}$), repeating step (a), and
   if the ratio is greater than the threshold value ($SW_{CH4}$), generating a $CH_4$ present signal.

2. The method of claim 1 wherein the sensor temperature is increased by increasing a heating voltage across the sensor.

3. The method of claim 1 wherein the elapsed time between the first time ($t_1$) and the second time ($t_2$) is about 5 minutes.

4. The method of claim 1 wherein the elapsed time between the first time ($t_1$) and the second time ($t_2$) is less than 5 minutes.

5. The method of claim 1 wherein the elapsed time between the first time ($t_1$) and the second time ($t_2$) is about 30 seconds.

6. The method of claim 1 wherein the $CH_4$ present signal is an alarm.

7. The method of claim 6 wherein the alarm is turned off if the ratio falls below the second threshold value ($SW_{CH4}$).

8. The method of claim 6 wherein the alarm must be turned off manually.

9. A method for detecting $CH_4$ with a $Ga_2O_3$ sensor comprising the following steps:
   (a) operating the sensor at a first temperature ($\theta 1$) and generating a sensor signal ($G_S$),
   (b) comparing the sensor signal ($G_S$) with a first threshold value ($SW_{EtOH}$),
   (c) if the sensor signal ($G_S$) is less than the first threshold value ($SW_{EtOH}$), repeating step (a) and,
   if the sensor signal ($G_S$) is greater than the first threshold value ($SW_{EtOH}$), executing step (d),
   (d) increasing the temperature of the sensor thereby altering the sensor signal ($G_S$),
   (e) differentiating the sensor signal ($G_S$) by means of an operational amplifier,
   (f) comparing the differentiated sensor signal with a second threshold value ($SW_{CH4}$),
   (g) if the differentiated sensor signal is less than the second threshold value ($SW_{CH4}$), repeating step (a), and
   if the differentiated sensor signal is greater than the second threshold value ($SW_{CH4}$), generating a $CH_4$ present signal.

10. The method of claim 9 wherein the sensor temperature is increased by increasing a heating voltage across the sensor.

11. The method of claim 9 wherein the $CH_4$ present signal is an alarm.

12. The method of claim 11 wherein the alarm is turned off if the differentiated signal falls below the second threshold value ($SW_{CH4}$).

13. The method of claim 11 wherein the alarm must be turned off manually.

14. A method for measuring the $CH_4$ concentration in a gas mixture with a $Ga_2O_3$ sensor, the method comprising the following steps:
   (a) operating the sensor at a first temperature ($\theta 1$),
   (b) generating and recording a first sensor signal ($G_S$),
   (c) increasing the temperature of the sensor to a second temperature ($\theta 2$),
   (d) generating a second sensor signal ($G(t_2)$),
   (e) calculating a ratio of the second sensor signal ($G(t_2)$) to the first sensor signal ($G_S$),
   (f) retrieving a $CH_4$ concentration associated with the ratio and with the second sensor signal ($G(t_2)$) from a stored set of values.

15. The method of claim 14 wherein the sensor temperature is increased by increasing a heating voltage across the sensor.

16. The method of claim 14 wherein the stored set of values is a graphical plot of $CH_4$ concentration as a function of both the second sensor signal ($G(t_2)$) and the ratio.

17. The method of claim 14 wherein the stored set of values is stored on an EEPROM.

* * * * *